US012780862B2

(12) United States Patent
Wang et al.

(10) Patent No.: US 12,780,862 B2
(45) Date of Patent: Nov. 3, 2026

(54) METHYL FRUCTOSIDE POLYETHER AMINE, PREPARATION METHOD THEREFOR AND USE THEREOF

(71) Applicants: Zhejiang Huangma Technology Co., Ltd., Shaoxing (CN); Zhejiang Lukean Chemical Co., Ltd., Shaoxing (CN); ZHEJIANG HUANGMA CHEMICAL NEW POLYMER MATERIAL CO., LTD, Shaoxing (CN); Zhejiang Huangma Shangyi New Material Co., Ltd., Shaoxing (CN)

(72) Inventors: Weisong Wang, Shaoxing (CN); Jiang Yu, Shaoxing (CN); Majishi Wang, Shaoxing (CN); Yifeng Jin, Shaoxing (CN)

(73) Assignees: Zhejiang Huangma Technology Co., Ltd., Shaoxing (CN); Zhejiang Lukean Chemical Co., Ltd., Shaoxing (CN); ZHEJIANG HUANGMA CHEMICAL NEW POLYMER MATERIAL CO., LTD, Shaoxing (CN); Zhejiang Huangma Shangyi New Material Co., Ltd., Shaoxing (CN)

( * ) Notice: Subject to any disclaimer, the term of this patent is extended or adjusted under 35 U.S.C. 154(b) by 357 days.

(21) Appl. No.: 18/676,542

(22) Filed: May 29, 2024

(65) Prior Publication Data

US 2025/0066406 A1 Feb. 27, 2025

(30) Foreign Application Priority Data

Jul. 20, 2023 (CN) ........................ 202310896054.X

(51) Int. Cl.
*C07H 1/00* (2006.01)
*B01J 23/44* (2006.01)
*B01J 35/00* (2024.01)
*C07H 7/02* (2006.01)

(52) U.S. Cl.
CPC ................ *C07H 1/00* (2013.01); *B01J 23/44* (2013.01); *B01J 35/19* (2024.01); *C07H 7/02* (2013.01)

(58) Field of Classification Search
CPC ............. C07H 1/00; C07H 15/08; C07H 7/02
See application file for complete search history.

(56) References Cited

FOREIGN PATENT DOCUMENTS

CN 116253767 A 6/2023

OTHER PUBLICATIONS

Fang, Lianshun, Synthesis of an alkyl glycoside polyoxyvinyl ether, Energy Chemical Industry, Apr. 1, 2017, pp. 26-28, vol. 38, No. 1.
Zou, Lixia et al., Study of hydroxypropyl high amylose by microemulsification, Food Science and Technology, 2005, pp. 9-12, No. 8.
Wen, Bin et al., Study on synthesis of methyl glucoside polyoxyethylene ether (I)-solvent-free synthesis, Journal of Xinjiang Petroleum Institute, Jun. 2001, vol. 13, No. 2.

*Primary Examiner* — Layla D Berry

(57) ABSTRACT

The present invention provides a methyl fructoside polyether amine, a preparation method therefor and use thereof, According to the methyl fructoside polyether amine, as a derivative of an alkyl glycoside, provided by the present invention, polyoxyethylene or polyoxypropylene chain links are introduced on the basis of retaining the advantages of safety, no toxicity, no irritation to skin, good biodegradability, good compatibility and the like of the alkyl glycoside, so that the water solubility, flowability and hard water resistance of a product are improved. The methyl fructoside polyether amine has a more excellent emulsifying property, meets the requirements of “green” and “environmental protection”, can be used as an emulsifier, a detergent, a foaming agent, a humectant, a thickening agent, a wetting agent, a dispersing agent, a penetrating agent and the like, and is widely used in the daily chemical industry, especially in the field of detergents.

20 Claims, No Drawings

METHYL FRUCTOSIDE POLYETHER AMINE, PREPARATION METHOD THEREFOR AND USE THEREOF

CROSS-REFERENCE TO RELATED APPLICATION

The present application claims priority from Chinese Patent Application No. 202310896054.X filed on Jul. 20, 2023, the contents of which are incorporated herein by reference in their entirety.

TECHNICAL FIELD

The present invention relates to the technical field of preparation of organic high-molecular compounds, and specifically relates to a methyl fructoside polyether amine, a preparation method therefor and use thereof.

BACKGROUND

Surfactants, as novel chemicals emerging in the 1950s, have fixed hydrophilic and lipophilic groups, which can significantly reduce the surface tension after directional arrangement on surfaces of solutions. The surfactants have a special status in industry, and are known as “industrial monosodium glutamate”. In the 21st century, the surfactants have been widely used in various fields of life and production, so that production efficiency is greatly improved, economic development is promoted, and great convenience is brought to people’s life. However, with extensive use of the surfactants, harm caused to the human body and pollution caused to the ecological environment are also increasing. With continuous improvement of the quality of people’s life and continuous increase of ecological environment requirements, “green chemistry” has become a hot spot of concern, and the development of environmentally friendly green surfactants has become an irresistable trend.

Polyether amines, as one of two major raw materials for the synthesis of polyurethane materials, are used in a largest amount in the polyurethane industry and have great market potential. With gradual depletion of petrochemical energy, traditional polyether amines, such as ethylene glycol polyether amine, methanol polyether amine and trimethylolpropane polyether amine, not only have the problem of raw material shortage, but also hinder a sustainable development path of the polyether amine industry due to pollution caused to the environment during production and use. Therefore, the use of environmentally friendly renewable resources to replace petroleum resources has become a biggest research hot spot. Alkyl glucoside polyether amines, as novel green and environmentally friendly renewable surfactants, are processed by using natural product starch or glucose as a raw material, which also have the special advantages of naturality, mildness, ecological safety, resource renewability, easy biodegradation and the like in addition to retaining excellent properties of traditional surfactants.

At present, no patents or documents have been disclosed to introduce preparation methods and use of the alkyl glycoside polyether amines, and most of documents and patents only introduce synthesis and use of glycoside polyethers. For example, in Synthesis of Alkyl Glycoside Polyoxyethylene Ether reported by Fang Lianshun, alkyl glycoside polyoxyethylene ether is synthesized by a solvent method using alkyl glycoside and ethylene oxide as raw materials and potassium hydroxide as a catalyst, the product is subjected to neutralizeation and decolorization, and five solvents, such as glycerol, dimethyl sulfoxide, ethylene glycol dimethyl ether, diethylene glycol dimethyl ether and polyethylene glycol dimethyl ether, are tested. Results show that the diethylene glycol dimethyl ether not only can dissolve the alkyl glycoside effectively and reduce the melting point, but also have a lower boiling point and is easy to remove, which is the most ideal solvent. Moreover, properties of the product are tested. It is found that suitable surface tension and wettability are achieved when an EO adduct number is 10-15. In Study on Synthesis of Hydroxypropyl High Amylose Starch by Microemulsification Method reported by Zhou Lixia et al., hydroxypropyl high amylose starch is synthesized by a microemulsification method using corn starch and propylene oxide as raw materials and acetone as a dispersing agent. Compared with an organic solvent method under same conditions, the hydroxypropyl high amylose starch has a higher product substitution degree, a lower gelatinization temperature and higher light transmittance, and can be used as a photodegradable film to replace traditional plastic bags. In Study on Synthesis Technology of Methyl Glucoside Polyoxyethylene Ether (1)—Solvent-free Synthesis reported by Wen Bin et al., methyl glucoside polyoxyethylene ether is synthesized by a solvent-free method, and sodium hydroxide and potassium hydroxide are compared in catalytic activity. Compared with a solvent method, the reaction temperature is increased, which is conducive to shortening the reaction induction period and increasing the reaction rate. However, with increase of the temperature, continuous heat release leads to temperature runaway, further leading to uncontrolled temperature and increased generation of byproducts. In view of the situations, it is urgent to develop a novel green and environmentally friendly renewable alkyl glycoside polyether amine, to use as a surfactant in various fields of life and production, especially in the detergent industry.

SUMMARY

The purpose of the present invention is to provide a methyl fructoside polyether amine, a preparation method therefor and use thereof. The methyl fructoside polyether amine provided by the present invention has safety, no toxicity and an excellent emulsifying property.

In order to achieve the purpose of the present invention, the present invention provides the following technical solutions.

A methyl fructoside polyether amine is provided. The methyl fructoside polyether amine has a structure as shown in a formula 1:

Formula 1

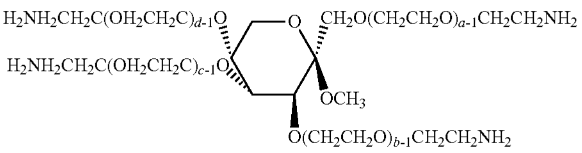

where a-d are independently an integer of 3-10; and a+b+c+d is an integer of 15-35.

The present invention further provides a preparation method for the methyl fructoside polyether amine as described in the above technical solution. The preparation method includes the following steps:

enabling methyl fructoside, alkylene oxide, a phase transfer catalyst and an alkali catalyst to carry out a polymerization reaction to obtain methyl fructoside polyether;

and enabling the methyl fructoside polyether, an aminating agent and a palladium on carbon catalyst to carry out a hydroamination reaction to obtain the methyl fructoside polyether amine.

Preferably, a preparation method for the methyl fructoside includes: enabling anhydrous fructose, anhydrous methanol and an acid catalyst to carry out a methylation reaction to obtain the methyl fructoside.

Preferably, a molar ratio of the anhydrous fructose to the anhydrous methanol is 1:(1-1.2); the acid catalyst includes one or more of sulfuric acid, hydrochloric acid and p-toluenesulfonic acid; and a mass of the acid catalyst is 2-5% of a total mass of the anhydrous fructose and the anhydrous methanol.

The methylation reaction is carried out at a temperature of 60-80° C. for 3-12 h.

Preferably, the alkylene oxide is ethylene oxide or propylene oxide; and a molar ratio of the alkylene oxide to the methyl fructoside is (5-30):1.

Preferably, the alkali catalyst includes one or more of sodium methoxide, potassium methoxide and potassium hydroxide, and a mass of the alkali catalyst is 0.1-1.0% of a mass of the methyl fructoside.

The phase transfer catalyst includes one or more of diethylene glycol dimethyl ether, glycerol, modified glycerol and dimethyl sulfoxide, and a mass of the phase transfer catalyst is 0.5-2.0% of a mass of the methyl fructoside.

Preferably, the polymerization reaction is carried out at a temperature of 105-120° C. and a pressure of 0.1-0.3 MPa for 3-5 h.

Preferably, the aminating agent includes liquid ammonia or ethylenediamine; and a molar ratio of the aminating agent to the methyl fructoside polyether is (5-8):1.

A mass ratio of the methyl fructoside polyether to the palladium on carbon catalyst is 1:(0.1-0.15).

Preferably, the hydroamination reaction is carried out at a temperature of 170-180° C. and a pressure of 10-12 MPa for 6-8 h.

The present invention further provides use of the methyl fructoside polyether amine as described in the above technical solution and a methyl fructoside polyether amine prepared by the preparation method as described in the above technical solution in detergents.

The present invention provides a methyl fructoside polyether amine. The methyl fructoside polyether amine has a structure as shown in a formula 1:

Formula 1

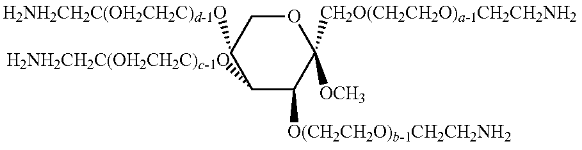

where a-d are independently an integer of 3-10; and a+b+c+d is an integer of 15-35. According to the methyl fructoside polyether amine, as a derivative of an alkyl glycoside, provided by the present invention, polyoxyethylene or polyoxypropylene chain links are introduced on the basis of retaining the advantages of safety, no toxicity, no irritation to skin, good biodegradability, good compatibility and the like of the alkyl glycoside, so that the water solubility, flowability and hard water resistance of a product are improved. The methyl fructoside polyether amine has more excellent emulsifying and moisturizing properties, meets the requirements of "green" and "environmental protection", can be used as an emulsifier, a detergent, a foaming agent, a humectant, a thickening agent, a wetting agent, a dispersing agent, a penetrating agent and the like, and is widely used in the daily chemical industry, especially in the field of detergents.

In addition, a preparation process of the methyl fructoside polyether amine of the present invention has no consumption of petroleum, coal and other resources and has a low cost.

DETAILED DESCRIPTION OF THE EMBODIMENTS

The present invention provides a methyl fructoside polyether amine. The methyl fructoside polyether amine has a structure as shown in a formula 1:

Formula 1

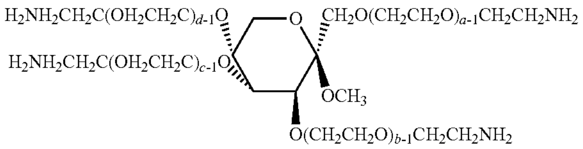

where a-d are independently an integer of 3-10; and a+b+c+d is an integer of 15-35.

In the present invention, the a-d are independently an integer of 3-10, preferably an integer of 5-8, and more preferably an integer of 6-7; the a+b+c+d is an integer of 15-35, preferably an integer of 20-30, and more preferably 25.

According to the methyl fructoside polyether amine, as a derivative of an alkyl glycoside, provided by the present invention, polyoxyethylene or polyoxypropylene chain links are introduced on the basis of retaining the advantages of safety, no toxicity, no irritation to skin, good biodegradability, good compatibility and the like of the alkyl glycoside, so that the water solubility, flowability and hard water resistance of a product are improved. The methyl fructoside polyether amine has a more excellent emulsifying property, meets the requirements of "green" and "environmental protection", can be used as an emulsifier, a detergent, a foaming agent, a humectant, a thickening agent, a wetting agent, a dispersing agent, a penetrating agent and the like, and is widely used in the daily chemical industry, especially in the field of detergents.

Moreover, compared with traditional aliphatic polyether amines, such as ethylene glycol polyether amine, methanol polyether amine and trimethylolpropane polyether amine, the methyl fructoside polyether amine has the advantages of safety, no toxicity, no irritation to skin, good compatibility and the like, can be biodegraded into small molecules such as water and carbon dioxide to enter a circulation system of nature again after waste, and meets development requirements of environmentally friendly materials. Compared with commonly used glucoside polyethers, the methyl fructoside polyether amine can react with a variety of compounds, such as compounds with an epoxy group and an isocyanate group, due to stronger reactivity of amino hydrogen at a terminal than hydroxyl hydrogen at a terminal of a polyether. Compared with glucoside polyethers, the methyl fructoside polyether amine has a wider use range in the industrial field. As an additive in detergents, the methyl fructoside polyether amine has lower surface tension, a stronger foaming property and hard water stability.

The present invention further provides a preparation method for the methyl fructoside polyether amine as described in the above technical solution. The preparation method includes the following steps:

enabling methyl fructoside, alkylene oxide, a phase transfer catalyst and an alkali catalyst to carry out a polymerization reaction to obtain methyl fructoside polyether;

and enabling the methyl fructoside polyether, an aminating agent and a palladium on carbon catalyst to carry out a hydroamination reaction to obtain the methyl fructoside polyether amine.

In the present invention, unless otherwise specified, all raw materials for preparation are commercially available commodities well known to persons skilled in the art.

In the present invention, the methyl fructoside, the alkylene oxide, the phase transfer catalyst and the alkali catalyst are enabled to carry out the polymerization reaction to obtain the methyl fructoside polyether.

In the present invention, a preparation method for the methyl fructoside preferably includes: enabling anhydrous fructose, anhydrous methanol and an acid catalyst to carry out a methylation reaction to obtain the methyl fructoside.

In the present invention, a molar ratio of the anhydrous fructose to the anhydrous methanol is preferably 1:(1-1.2), more preferably 1:(1-1.1); the acid catalyst preferably includes one or more of sulfuric acid, hydrochloric acid and p-toluenesulfonic acid, more preferably includes sulfuric acid and/or hydrochloric acid, and most preferably includes sulfuric acid; when the acid catalyst includes two or more of the above specific choices, proportioning of the acid catalyst is not particularly limited in the present invention; a concentration of the acid catalyst is preferably 20-40%, more preferably 25-35%, and most preferably 30%; and a mass of the acid catalyst is preferably 2-5% of a total mass of the anhydrous fructose and the anhydrous methanol, more preferably 2-4%, and most preferably 2-3%.

In the present invention, the methylation reaction is preferably carried out at a temperature of 60-80° C., more preferably 65-75° C., and most preferably 70° C.; and a reaction time is preferably 3-12 h, more preferably 3-10 h, and most preferably 3-8 h. Specifically, the reaction time may be adjusted according to different catalysts. In the present invention, the temperature is preferably raised from room temperature to the methylation reaction temperature at a heating rate of 1.0-2.5° C./min, more preferably 1.3-2.0° C./min, and most preferably 1.5-1.8° C./min. In the present invention, the methylation reaction is preferably carried out in an inert gas atmosphere, and the inert gas is preferably nitrogen, helium or argon.

In the present invention, the methyl fructoside is directly synthesized by the methylation reaction. The methyl fructoside is produced by the reaction of a hemiacetal hydroxyl group of the fructose and the methanol under the action of the acid catalyst.

In the present invention, the preparation method further preferably includes: after the methylation reaction, sequentially subjecting a crude product of methyl fructoside obtained by the reaction to cooling, first neutralization, drying, dehydration and dealcoholization.

In the present invention, a temperature after the cooling is preferably 20-45° C., more preferably 30-40° C. In the present invention, a cooling method and a cooling rate are not particularly limited, and a method well known to persons skilled in the art may be used.

In the present invention, a reagent used in the first neutralization is preferably a neutralizing alkali solution; a solvent of the neutralizing alkali solution is preferably methanol; a solute preferably includes potassium hydroxide, sodium hydroxide, sodium methoxide or sodium ethoxidel, more preferably includes sodium hydroxide, sodium methoxide or sodium ethoxide, and most preferably includes sodium hydroxide and/or sodium methoxide; when the solute includes two or more of the above specific choices, proportioning of the solute is not particularly limited in the present invention; a mass percentage content of the solute is preferably 50-80%, more preferably 60-80%, and most preferably 70-80%; and a mass of the neutralizing alkali solution is preferably 2-5% of a total mass of the anhydrous fructose and the anhydrous methanol, more preferably 3-5%, and most preferably 4.5%.

In the present invention, the first neutralization is used for preventing hydrolysis of the methyl fructoside.

In the present invention, a drying method is preferably vacuum drying; and a vacuum drying process is not particularly limited in the present invention, and a method well known to persons skilled in the art may be used.

In the present invention, dehydration and dealcoholization methods are not particularly limited, and methods well known to persons skilled in the art may be used.

In the present invention, the alkylene oxide is preferably ethylene oxide or propylene oxide. In the present invention, a molar ratio of the alkylene oxide to the methyl fructoside is preferably (5-30):1, more preferably (10-30):1, and most preferably (10-25):1.

In the present invention, the alkali catalyst preferably includes one or more of sodium methoxide, potassium methoxide and potassium hydroxide, more preferably includes sodium methoxide and/or potassium hydroxide, and most preferably includes potassium hydroxide; when the alkali catalyst includes two or more of the above specific choices, proportioning of the alkali catalyst is not particularly limited in the present invention; and a mass of the alkali catalyst is preferably 0.1-1.0% of a mass of the methyl fructoside, more preferably 0.2-0.8%, and most preferably 0.4-0.6%.

In the present invention, the phase transfer catalyst preferably includes one or more of diethylene glycol dimethyl ether, glycerol, modified glycerol and dimethyl sulfoxide, more preferably includes one or more of diethylene glycol dimethyl ether, modified glycerol and dimethyl sulfoxide, and most preferably includes diethylene glycol dimethyl ether and/or modified glycerol; when the phase transfer catalyst includes two or more of the above specific choices, proportioning of the phase transfer catalyst is not particularly limited in the present invention; and a mass of the phase transfer catalyst is preferably 0.5-2.0% of a mass of the methyl fructoside, more preferably 0.8-1.8%, and most preferably 1.0-1.5%.

In the present invention, the preparation method further preferably includes: before the polymerization reaction, mixing the methyl fructoside, the phase transfer catalyst and the alkali catalyst and then introducing the alkylene oxide; the mixing is preferably stirring; a stirring process is not particularly limited in the present invention, and a method well known to persons skilled in the art may be used; and the alkylene oxide is preferably introduced at a rate of 200-600 g/h, more preferably 250-500 g/h, and most preferably 250-450 g/h.

In the present invention, the polymerization reaction is preferably carried out at a temperature of 105-120° C., more preferably 105-115° C., and most preferably 110-115° C.; the polymerization reaction is preferably carried out at a pressure of 0.1-0.3 MPa, more preferably 0.15-0.25 MPa, and most preferably 0.2 MPa; the polymerization reaction is preferably carried out for 3-5 h, more preferably 3.5-4.5 h, and most preferably 4 h; specifically, the polymerization reaction is carried out until the pressure in a reactor is not reduced any more within 30 min; the polymerization reaction is carried out under stirring conditions; and a stirring process is not particularly limited in the present invention, and a method well known to persons skilled in the art may be used.

In the present invention, the preparation method further preferably includes: after the polymerization reaction, sequentially subjecting a crude product of methyl fructoside polyether obtained by the reaction to second neutralization, dilution, decolorization, first adsorption and first filtration to obtain the methyl fructoside polyether. In the present invention, a reagent used in the second neutralization is preferably a neutralizing acid solution; a solute of the neutralizing acid solution preferably includes one or more of phosphoric acid, hydrochloric acid and sulfuric acid, more preferably includes hydrochloric acid and/or sulfuric acid, and most preferably includes sulfuric acid; when the solute includes two or more of the above specific choices, proportioning of the solute is not particularly limited in the present invention; a concentration is preferably 20-40%, more preferably 25-35%, and most preferably 30%; and an amount of the neutralizing acid solution is preferably 0.5-1.0% of a mass of the crude product of methyl fructoside polyether, more preferably 0.8-1.0%.

In the present invention, a diluent used in the dilution is preferably ethanol. An amount of the diluent is 4.0-5.0% of a mass of the crude product of methyl fructoside polyether, more preferably 4.2-4.8%.

In the present invention, a decolorizing agent used in the decolorization is activated carbon; and an amount of the decolorizing agent is 1.0-3.0% of the mass of the crude product of methyl fructoside polyether, more preferably 1.5-2.5%.

In the present invention, an adsorbent used in the first adsorption preferably includes one or more of chromatographic silica gel, a molecular sieve and diatomite, and more preferably includes chromatographic silica gel and/or diatomite; when the adsorbent includes two or more of the above specific choices, proportioning of the adsorbent is not particularly limited in the present invention; and an adsorption process is not particularly limited in the present invention, and a method well known to persons skilled in the art may be used.

In the present invention, a first filtration method is not particularly limited, and a method well known to persons skilled in the art may be used.

After the methyl fructoside polyether is obtained, the methyl fructoside polyether, the aminating agent and the palladium on carbon catalyst are enabled to carry out the hydroamination reaction to obtain the methyl fructoside polyether amine in the present invention.

In the present invention, the aminating agent preferably includes liquid ammonia or ethylenediamine, and more preferably includes liquid ammonia; and a molar ratio of the aminating agent to the methyl fructoside polyether is preferably (5-8):1, more preferably (6-7):1.

In the present invention, a mass ratio of the methyl fructoside polyether to the palladium on carbon catalyst is preferably 1:(0.1-0.15), more preferably 1:(0.11-0.14).

In the present invention, the methyl fructoside polyether is preferably added by a raw material booster pump, and a space velocity of the raw material booster pump is preferably 0.1-0.2 $h^{-1}$, more preferably 0.15 $h^{-1}$.

In the present invention, the liquid nitrogen is preferably added by a liquid nitrogen booster pump, and a space velocity of the liquid nitrogen booster pump is preferably 0.15-0.3 $h^{-1}$, more preferably 0.25 $h^{-1}$.

In the present invention, the hydroamination reaction is preferably carried out at a temperature of 170-180° C., more preferably 172-178° C.; a pressure is preferably 10-12 MPa, more preferably 10-11 MPa; a time is preferably 6-8 h, more preferably 6.5-7.5 h; a device used in the hydroamination reaction is preferably a continuous fixed bed; the hydroamination reaction is preferably carried out in a hydrogen atmosphere; and the hydrogen is preferably added by a hydrogen booster pump.

In the present invention, the hydroamination reaction is carried out by a direct catalytic reduction amination method under the catalysis of the palladium on carbon catalyst to obtain the methyl fructoside polyether amine.

In the present invention, the preparation method further preferably includes: after the hydroamination reaction, sequentially subjecting a crude product of methyl fructoside polyether amine obtained by the reaction to second adsorption, second filtration, denitrification and dehydration to obtain the methyl fructoside polyether amine.

In the present invention, methods for the second adsorption, the second filtration, the denitrification and the dehydration are not particularly limited, and methods well known to persons skilled in the art may be used.

The preparation method provided by the present invention has clean and renewable raw materials, wide distribution of resources, no consumption of petroleum, coal and other resources, and a low cost.

The present invention further provides use of the methyl fructoside polyether amine as described in the above technical solution and a methyl fructoside polyether amine prepared by the preparation method as described in the above technical solution in detergents.

In the present invention, a use method of the methyl fructoside polyether amine in detergents is not particularly limited, and a method well known to persons skilled in the art may be used.

In the present invention, the methyl fructoside polyether amine added to a detergent can effectively reduce surface tension and interfacial tension, can achieve the effects of foaming, moisturizing, skin moistening, luster improving and the like, and is a multi-functional additive.

In order to further illustrate the present invention, the methyl fructoside polyether amine provided by the present invention is described in detail below in combination with examples, but the examples shall not be understood as limiting the scope of protection of the present invention.

Example 1

170 g of anhydrous fructose, 32 g of anhydrous methanol and 4 g of 30% sulfuric acid were added to a four-necked flask, heated to 70° C. at a heating rate of 1.5° C./min to carry out a methylation reaction in a nitrogen atmosphere for 3 h and then cooled to 35° C., 8 g of a methanol solution of sodium methoxide, with a concentration of 70%, was added to adjust the pH value to 8, and then vacuum drying, dehydration and dealcoholization were performed to obtain methyl fructoside.

200 g of the methyl fructoside, 1 g of potassium hydroxide and 2 g of modified glycerol were added to a stirring reactor and stirred in a nitrogen atmosphere at 105° C., 880 g of ethylene oxide with an adduct number of 20 was introduced within 3 h, a polymerization reaction was carried out at 0.20 MPa at 115° C. for 4 h until the pressure in the reactor was not reduced any more within 30 min, and then degassing and discharging were performed to obtain a crude product of methyl fructoside polyether. 10.8 g of sulfuric acid with a concentration of 30% was added for neutralizing the crude product of methyl fructoside polyether until the pH value was 7.5, then 50 g of ethanol was added for dilution, 20 g of activated carbon was added for decolorization, adsorption was performed with chromatographic silica gel, and filtration was performed to obtain 1,080 g of methyl fructoside polyether.

120 g of a palladium on carbon catalyst was added to a fixed bed reactor, 1,080 g of the methyl fructoside polyether was pumped by a raw material booster pump at a space velocity of 0.1 $h^{-1}$, 1,620 g of liquid ammonia was pumped by a liquid ammonia booster pump at a space velocity of 0.15 $h^{-1}$, hydrogen was pumped by a hydrogen booster pump, and a hydroamination reaction was carried out in a hydrogen atmosphere at 170° C. and 10.0 MPa for 8 h to obtain a crude product of methyl fructoside polyether amine. The crude product of methyl fructoside polyether amine was sequentially subjected to adsorption, filtration, denitrification and dehydration to obtain methyl fructoside polyether amine.

Chemical equations involved in Example 1 are shown in a formula I.

Formula I

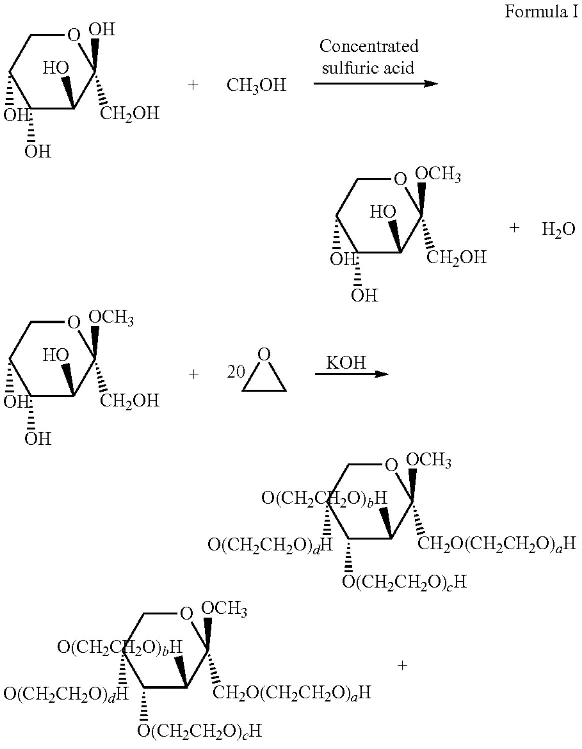

-continued

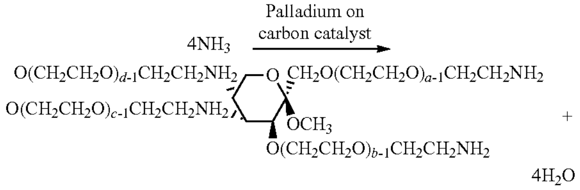

a + b + c + d = 20

Example 2

170 g of anhydrous fructose, 32 g of anhydrous methanol and 5 g of 25% p-toluenesulfonic acid were added to a four-necked flask, heated to 60° C. at a heating rate of 1.3° C./min to carry out a methylation reaction in a nitrogen atmosphere for 8 h and then cooled to 40° C., 8.5 g of a methanol solution of sodium hydroxide, with a concentration of 70%, was added to adjust the pH value to 9, and then vacuum drying, dehydration and dealcoholization were performed to obtain methyl fructoside.

200 g of the methyl fructoside, 1.5 g of sodium methoxide and 3 g of diethylene glycol dimethyl ether were added to a stirring reactor and stirred in an argon atmosphere at 105° C., 870 g of propylene oxide with an adduct number of 15 was introduced within 2 h, a polymerization reaction was carried out at 0.20 MPa at 115° C. for 4 h until the pressure in the reactor was not reduced any more within 30 min, and then degassing and discharging were performed to obtain a crude product of methyl fructoside polyether. 10 g of sulfuric acid with a concentration of 25% was added for neutralizing the crude product of methyl fructoside polyether until the pH value was 7.5, then 45 g of ethanol was added for dilution, 15 g of activated carbon was added for decolorization, adsorption was performed with diatomite, and filtration was performed to obtain 1,070 g of methyl fructoside polyether.

130 g of a palladium on carbon catalyst was added to a fixed bed reactor, 1,070 g of the methyl fructoside polyether was pumped by a raw material booster pump at a space velocity of 0.2 $h^{-1}$, 1,605 g of liquid ammonia was pumped by a liquid ammonia booster pump at a space velocity of 0.3 $h^{-1}$, hydrogen was pumped by a hydrogen booster pump, and a hydroamination reaction was carried out in a hydrogen atmosphere at 180° C. and 12.0 MPa for 7 h to obtain a crude product of methyl fructoside polyether amine. The crude product of methyl fructoside polyether amine was sequentially subjected to adsorption, filtration, denitrification and dehydration to obtain methyl fructoside polyether amine.

Chemical equations involved in Example 2 are shown in a formula II.

Formula II

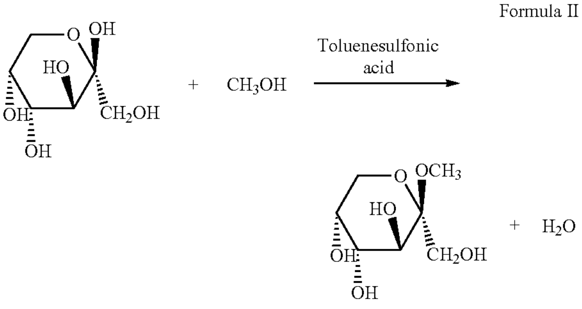

-continued

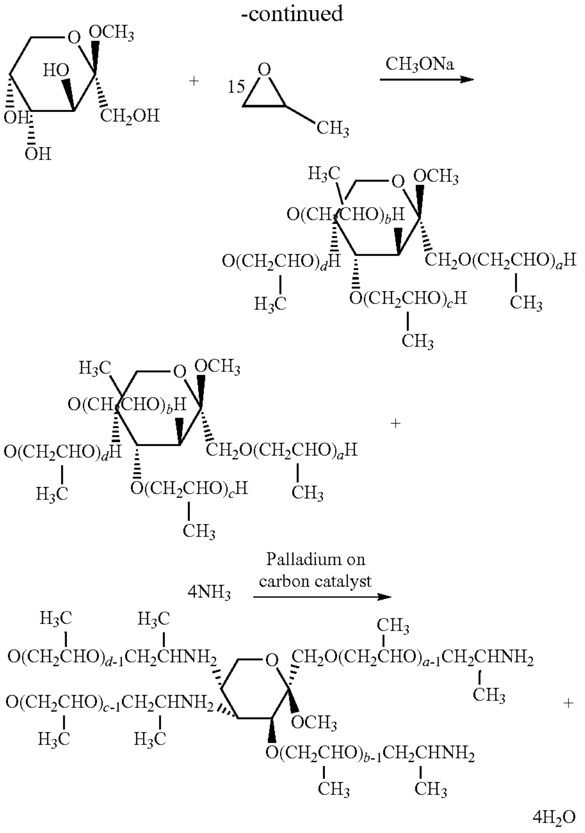

a + b + c + d = 15

Example 3

165 g of anhydrous fructose, 38 g of anhydrous methanol and 4 g of 25% hydrochloric acid were added to a four-necked flask, heated to 80° C. at a heating rate of 1.8° C./min to carry out a methylation reaction in a nitrogen atmosphere for 12 h and then cooled to 30° C., 8 g of a methanol solution of sodium ethoxide, with a concentration of 75%, was added to adjust the pH value to 8.5, and then vacuum drying, dehydration and dealcoholization were performed to obtain methyl fructoside.

200 g of the methyl fructoside, 1 g of potassium methoxide and 2.5 g of dimethyl sulfoxide were added to a stirring reactor and stirred in a helium atmosphere at 105° C., 1,320 g of ethylene oxide with an adduct number of 30 was introduced within 4 h, a polymerization reaction was carried out at 0.20 MPa at 115° C. for 3 h until the pressure in the reactor was not reduced any more within 30 min, and then degassing and discharging were performed to obtain a crude product of methyl fructoside polyether. 15 g of sulfuric acid with a concentration of 25% was added for neutralizing the crude product of methyl fructoside polyether until the pH value was 7, then 60 g of ethanol was added for dilution, 30 g of activated carbon was added for decolorization, adsorption was performed with a molecular sieve, and filtration was performed to obtain 1,520 g of methyl fructoside polyether.

180 g of a palladium on carbon catalyst was added to a fixed bed reactor, 1,520 g of the methyl fructoside polyether was pumped by a raw material booster pump at a space velocity of $0.15\ h^{-1}$, 2,533 g of liquid ammonia was pumped by a liquid ammonia booster pump at a space velocity of $0.25\ h^{-1}$, hydrogen was pumped by a hydrogen booster pump, and a hydroamination reaction was carried out in a hydrogen atmosphere at 175° C. and 11.0 MPa for 8 h to obtain a crude product of methyl fructoside polyether amine. The crude product of methyl fructoside polyether amine was sequentially subjected to adsorption, filtration, denitrification and dehydration to obtain methyl fructoside polyether amine.

Chemical equations involved in Example 3 are shown in a formula III.

Formula III

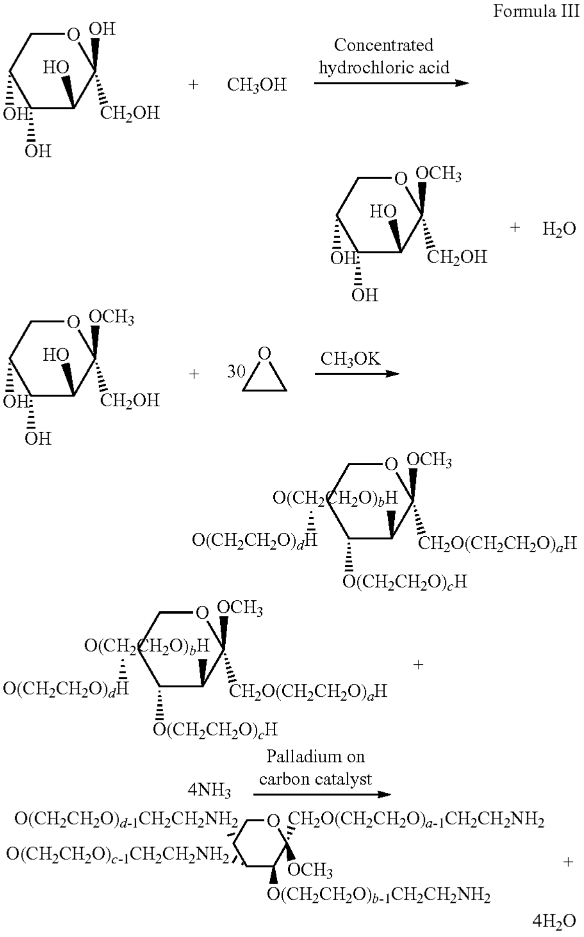

a + b + c + d = 30

Example 4

160 g of anhydrous fructose, 42 g of anhydrous methanol and 5 g of 30% sulfuric acid were added to a four-necked flask, heated to 70° C. at a heating rate of 1.5° C./min to carry out a methylation reaction in a nitrogen atmosphere for 3 h and then cooled to 40° C., 7 g of a methanol solution of potassium hydroxide, with a concentration of 80%, was added to adjust the pH value to 9, and then vacuum drying, dehydration and dealcoholization were performed to obtain methyl fructoside.

200 g of the methyl fructoside, 1 g of potassium hydroxide and 2 g of glycerol were added to a stirring reactor and stirred in a nitrogen atmosphere at 105° C., 440 g of ethylene oxide with an adduct number of 10 was introduced within 1.5 h, a polymerization reaction was carried out at 0.20 MPa at 115° C. for 4 h until the pressure in the reactor was not reduced any more within 30 min, and then degassing and discharging were performed to obtain a crude product of methyl fructoside polyether. 3 g of sulfuric acid with a concentration of 30% was added for neutralizing the crude product of methyl fructoside polyether until the pH value was 8, then 24 g of ethanol was added for dilution, 18 g of activated carbon was added for decolorization, chromatographic silica gel was used as an adsorbent, and filtration was performed to obtain 640 g of methyl fructoside polyether.

75 g of a palladium on carbon catalyst was added to a fixed bed reactor, 640 g of the methyl fructoside polyether was pumped by a raw material booster pump at a space velocity of 0.15 $h^{-1}$, 1,067 g of liquid ammonia was pumped by a liquid ammonia booster pump at a space velocity of 0.25 $h^{-1}$, hydrogen was pumped by a hydrogen booster pump, and a hydroamination reaction was carried out in a hydrogen atmosphere at 180° C. and 12.0 MPa for 6 h to obtain a crude product of methyl fructoside polyether amine. The crude product of methyl fructoside polyether amine was sequentially subjected to adsorption, filtration, denitrification and dehydration to obtain methyl fructoside polyether amine.

Chemical equations involved in Example 4 are shown in a formula IV.

Formula IV

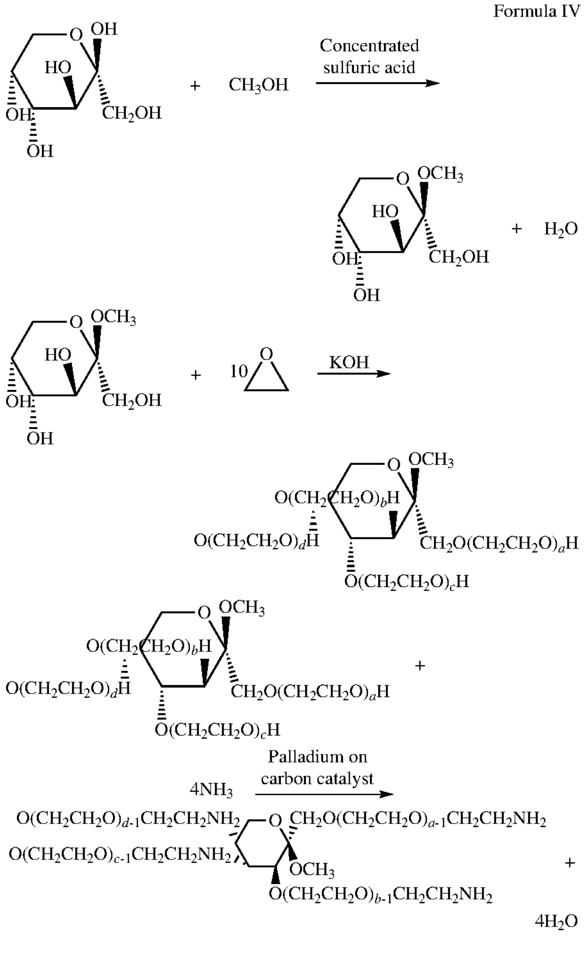

-continued a + b + c + d = 10

Test Example

According to GB/T12008.3-2009, hydroxyl values of the methyl fructoside polyether amines prepared in Examples 1-4 were determined, and molecular weights were deduced.

The methyl fructoside polyether amines prepared in Examples 1-4 were titrated with a 0.5 mol/L hydrochloric acid solution, and a total amine value of the methyl fructoside polyether amines was calculated based on a volume of the hydrochloric acid consumed.

Salicylaldehyde was enabled to react with primary amine and then titrated with hydrochloric acid, and a primary amine value of the methyl fructoside polyether amines was calculated by subtracting a secondary amine value and a tertiary amine value from the total amine value.

The amination conversion rate and the primary amine rate are calculated according to a formula (1) and a formula (2):

$$\text{amination conversion rate} = \text{total amine value}/\text{hydroxyl value} \times 100\% \text{ formula,} \quad (1)$$

$$\text{primary amine rate} = \text{primary amine value}/\text{total amine value} \times 100\% \text{ formula.} \quad (2)$$

Results are shown in Table 1.

Table 1 Reaction conversion rate and primary amine selectivity of methyl fructoside polyether amines in Examples 1-4

| | Reaction conversion rate (%) | Primary amine selectivity (%) |
|---|---|---|
| Example 1 | 97 | 98 |
| Example 2 | 95 | 97 |
| Example 3 | 96.5 | 98.5 |
| Example 4 | 98 | 99.5 |

As can be seen from the results in Table 1, the methyl fructoside polyether amine provided by the present invention has a reaction conversion rate of 95% or above and a primary amine selectivity of 99.5%. When the adduct number of the ethylene oxide is 10-20, the amination reaction conversion rate is higher, and the primary amine selectivity is also higher, so that the ethoxy series is easier to carry out the amination reaction than the propoxy series.

Samples were taken at regular intervals for testing for a total of 30 times. Experimental results are basically consistent with the above results and have good repeatability.

Application Example

The methyl fructoside polyether amines prepared in Examples 1-4 were added to a detergent (OMO clean full-effect laundry detergent purchased from Unilever), and properties were tested specifically as follows.

(1) Water solubility: 150 g of the detergent was dissolved in 100 g of water, and 200 g of the detergent was dissolved in 100 g of ethanol. The detergent has good water solubility, is easily dissolved in water and ethanol, and has good compatibility with other types of surfactants.

(2) Acid and alkali stability: After being soaked in an acid or alkali solution with a pH value of 1, 2, 13 or 14 at room temperature of 25° C. for 10 h, respectively, the appearance and properties of the detergent are not obviously changed, and the detergent has high chemical stability and is not affected by an acid and an alkali.

(3) Surface tension: The surface tension of the detergent was 30 mN/m as determined by a surface tension tester, the surface tension of the detergent was 35 mN/m as determined by a drop volume method, the surface tension of the detergent without addition of the methyl fructoside polyether amine was 50 mN/m as determined by a surface tension tester, and the surface tension of the detergent without addition of the methyl fructoside polyether amine was 55 mN/m as determined by a drop volume method. The results show that the detergent with addition of the methyl fructoside polyether amine has lower surface tension than the detergent without addition of the methyl fructoside polyether amine.

(4) Foaming property and foam stability: The foaming property and foam stability of detergents were determined by an electric conductivity method. Compared with the detergent without addition of the methyl fructoside polyether amine, the foaming time is shortened by half, and the foam stability is higher.

(5) Biodegradability: Detergents were biodegraded by a soil burial decomposition method. The soil burial decomposition method includes the following operation steps:

1, preparation of test materials: selecting samples with appropriate sizes to ensure that surfaces are smooth and are not polluted;

2, digging of trenches: digging trenches with depths in a use state in soil to be investigated;

3, placement of the samples: placing the conventionally prepared samples at various specified horizontal depths, and performing backfilling with soil according to technical requirements;

4, burying with requirements: burying the samples at a same depth, and covering the samples with a soil layer with a same thickness;

5, monitoring and recording: regularly monitoring degradation conditions of the materials, and recording relevant data, such as material quality changes, gas production and the like; and 6, data analysis: calculating the degradation rate and degree of the materials by comparing the data at different time points, so as to evaluate the biodegradability.

Results show that the detergent with addition of the methyl fructoside polyether amine has better biodegradability, and the propoxy series has better degradability than the ethoxy series.

(6) Flowability: The flowability of detergents was detected by an electromagnetic flowmeter. When a liquid flows through a pipe, a charge band in fluid drives the liquid to flow. The flow quantity of a conductive liquid flowing through an electrode can be calculated by detecting induced potential on the electrode. Compared with the detergent without addition of the methyl fructoside polyether amine, higher flowability is achieved.

(7) Hard water resistance: The hard water resistance of detergents was determined by a hardness titration method. First, a substance to be tested was mixed with an ethylenediamine tetraacetic acid (EDTA) solution with a known concentration, and then an indicator was added. When calcium and magnesium ions react completely with the EDTA, the color of the solution is changed, and the hard water resistance of the substance to be tested can be determined by comparing the degree of color change. Compared with the detergent without addition of the methyl fructoside polyether amine, higher hard water resistance is achieved.

(8) Emulsifying stability: The emulsifying stability was determined as follows: 1, preparation of samples: adding an emulsifier to deionized water in a certain proportion to prepare a solution with a quantitative concentration, and adding detergents to be tested; 2, continuous oscillation at a certain temperature in a laboratory: observing the stability of the emulsifier under certain temperature, time and oscillation conditions; and 3, observation of the emulsifying stability: observing the relative stability by naked eyes, and measuring a stability index with an instrument. Compared with the detergent without addition of the methyl fructoside polyether amine, a stronger emulsifying property is achieved.

Although the present invention is described in detail above through the examples, the examples are only a part of the examples of the present invention, rather than all of the examples. Other examples can also be obtained without creative effort according to the examples, and all the examples are within the scope of protection of the present invention.

What is claimed is:

1. A preparation method for a methyl fructoside polyether amine, wherein the methyl fructoside polyether amine has a structure as shown in a formula 1:

Formula 1

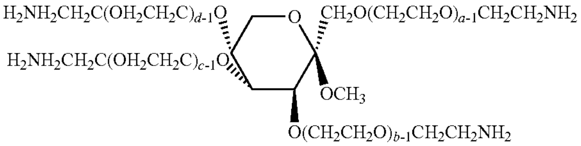

wherein a-d are independently an integer of 3-10; a+b+c+d is an integer of 15-35; and the preparation method comprises the following steps:

enabling methyl fructoside, alkylene oxide, a phase transfer catalyst and an alkali catalyst to carry out a polymerization reaction to obtain methyl fructoside polyether;

and enabling the methyl fructoside polyether, an aminating agent and a palladium on carbon catalyst to carry out a hydroamination reaction to obtain the methyl fructoside polyether amine.

2. The preparation method according to claim 1, wherein a preparation method for the methyl fructoside comprises: enabling anhydrous fructose, anhydrous methanol and an acid catalyst to carry out a methylation reaction to obtain the methyl fructoside.

3. The preparation method according to claim 2, wherein a molar ratio of the anhydrous fructose to the anhydrous methanol is 1:(1-1.2).

4. The preparation method according to claim 2, wherein the acid catalyst comprises one or more of sulfuric acid, hydrochloric acid and p-toluenesulfonic acid; and a mass of the acid catalyst is 2-5% of a total mass of the anhydrous fructose and the anhydrous methanol.

5. The preparation method according to claim 2, wherein the methylation reaction is carried out at a temperature of 60-80° C. for 3-12 h.

6. The preparation method according to claim 5, wherein the temperature is raised from room temperature to the methylation reaction temperature at a heating rate of 1.0-2.5° C./min.

7. The preparation method according to claim 2, wherein the methylation reaction is carried out in an inert gas atmosphere.

8. The preparation method according to claim 2, further comprising: after the methylation reaction, sequentially subjecting a crude product of methyl fructoside obtained by the reaction to cooling, first neutralization, drying, dehydration and dealcoholization.

9. The preparation method according to claim 8, wherein a reagent used in the first neutralization is a neutralizing alkali solution, and the neutralizing alkali solution comprises a methanol solution of potassium hydroxide, sodium hydroxide, sodium methoxide or sodium ethoxide; and an amount of the neutralizing alkali solution is 2-5% of a total mass of the anhydrous fructose and the anhydrous methanol.

10. The preparation method according to claim 1, wherein the alkylene oxide is ethylene oxide or propylene oxide; and a molar ratio of the alkylene oxide to the methyl fructoside is (5-30):1.

11. The preparation method according to claim 1, wherein the phase transfer catalyst comprises one or more of diethylene glycol dimethyl ether, glycerol, modified glycerol and dimethyl sulfoxide, and a mass of the phase transfer catalyst is 0.5-2.0% of a mass of the methyl fructoside.

12. The preparation method according to claim 1, wherein the alkali catalyst comprises one or more of sodium methoxide, potassium methoxide and potassium hydroxide, and a mass of the alkali catalyst is 0.1-1.0% of a mass of the methyl fructoside.

13. The preparation method according to claim 1, wherein the polymerization reaction is carried out at a temperature of 105-120° C. and a pressure of 0.1-0.3 MPa for 3-5 h.

14. The preparation method according to claim 1, further comprising: before the polymerization reaction, mixing the methyl fructoside, the phase transfer catalyst and the alkali catalyst and then introducing the alkylene oxide.

15. The preparation method according to claim 14, wherein the alkylene oxide is introduced at a rate of 200-600 g/h.

16. The preparation method according to claim 1, further comprising: after the polymerization reaction, sequentially subjecting a crude product of methyl fructoside polyether obtained by the reaction to second neutralization, dilution, decolorization, first adsorption and first filtration to obtain the methyl fructoside polyether.

17. The preparation method according to claim 16, wherein a reagent used in the second neutralization is a neutralizing acid solution, and the neutralizing acid solution comprises one or more of phosphoric acid, hydrochloric acid and sulfuric acid; and an amount of the neutralizing acid solution is 0.5-1.0% of a mass of the crude product of methyl fructoside polyether.

18. The preparation method according to claim 1, wherein the aminating agent comprises liquid ammonia or ethylenediamine; and a molar ratio of the aminating agent to the methyl fructoside polyether is (5-8):1.

19. The preparation method according to claim 1, wherein a mass ratio of the methyl fructoside polyether to the palladium on carbon catalyst is 1:(0.1-0.15).

20. The preparation method according to claim 1, wherein the hydroamination reaction is carried out at a temperature of 170-180° C. and a pressure of 10-12 MPa for 6-8 h.

* * * * *